United States Patent [19]

Janssens et al.

[11] Patent Number: 5,674,866
[45] Date of Patent: Oct. 7, 1997

[54] ANTIALLERGIC IMIDAZOAZEPINES

[75] Inventors: Frans Eduard Janssens, Bonheiden; Joseph Elisabeth Leenaerts, Rijkevorsel, both of Belgium

[73] Assignee: Janssen Pharmaceutica N.V., Beerse, Belgium

[21] Appl. No.: 557,131

[22] PCT Filed: Jul. 6, 1994

[86] PCT No.: PCT/EP94/02287

§ 371 Date: Dec. 13, 1995

§ 102(e) Date: Dec. 13, 1995

[87] PCT Pub. No.: WO95/02600

PCT Pub. Date: Jan. 26, 1995

[30] Foreign Application Priority Data

Jul. 13, 1993 [EP] European Pat. Off. .............. 93202154

[51] Int. Cl.$^6$ .............. A61K 31/55; C07D 487/04
[52] U.S. Cl. .............. 514/214; 540/522; 540/578; 540/579; 546/210; 514/215
[58] Field of Search .............. 540/522, 578, 540/579; 546/210; 514/214, 215

[56] References Cited

U.S. PATENT DOCUMENTS

| | | | |
|---|---|---|---|
| 5,461,050 | 10/1995 | Janssens et al. | 514/214 |
| 5,468,743 | 11/1995 | Janssens et al. | 514/214 |

FOREIGN PATENT DOCUMENTS

| | | | |
|---|---|---|---|
| 0 270 818 | 6/1988 | European Pat. Off. | 514/214 |
| 0 339 978 | 11/1989 | European Pat. Off. | 514/214 |
| WO 92/06981 | 4/1992 | WIPO | 514/214 |
| WO 92/06971 | 4/1992 | WIPO | 514/214 |

*Primary Examiner*—Robert T. Bond
*Attorney, Agent, or Firm*—Charles J. Metz

[57] ABSTRACT

The present invention is concerned with novel imidazoazepines of formula

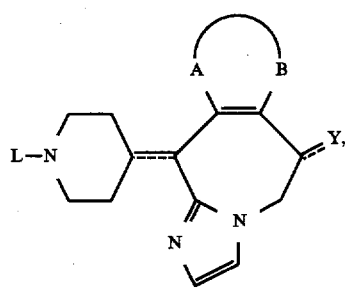

(I)

the pharmaceutically acceptable addition salts and stereochemically isomeric forms thereof, wherein each of the dotted lines independently represents an optional bond; —A—B— is a radical of formula —X—CH=CH— (a-1); —CH=CH—X— (a-2); or —CH=CH—CH=CH— (a-3); X represents O, S or NR$^1$; R$^1$ represents hydrogen or $C_{1-6}$alkyl; -----Y is a radical of formula =O (b-1); —OH (b-2); or =N—OH (b-3); and L represents hydrogen, $C_{1-4}$alkylcarbonyl, $C_{1-4}$alkyloxycarbonyl, phenylcarbonyl, $C_{1-6}$alkyl or $C_{1-6}$alkyl substituted with $C_{1-4}$alkyloxycarbonyl, hydroxycarbonyl, aryl, aryloxy or a radical of formula

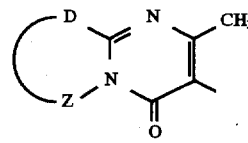

(c)

—D—Z— is —S—CH=CH—, —S—CH$_2$—CH$_2$—, —S—CH$_2$—CH$_2$—CH$_2$—, —CH=CH—CH=CH— or —CH$_2$—CH$_2$—CH$_2$—CH$_2$—; and aryl is phenyl or phenyl substituted with halo, hydroxy or $C_{1-4}$alkyloxy. Compositions comprising said compounds, processes for preparing the same and the use of these compounds for treating allergic diseases.

14 Claims, No Drawings

ANTIALLERGIC IMIDAZOAZEPINES

CROSS-REFERENCE TO RELATED APPLICATIONS

This application is based upon PCT Application Ser. No. PCT/EP 94/02287, filed Jul. 6, 1994, which claims priority from European Patent Application Ser. No. 93.202.154.6, filed on Jul. 13, 1993.

WO 92/22 551 and WO 92/22 553 describe imidazoazepines having antiallergic activity. In EP-0,339,978 there are described (benzo- or pyrido)cyclohepta heterocyclics which are useful as PAF antagonists, antihistaminics and/or anti-inflammatory agents. In WO 88/03 138 there are described benzo[5,6]cycloheptapyridines which possess antiallergic and anti-inflammatory activity.

The compounds of the present invention differ structurally from the cited art-known compounds by the fact that the central 7-membered ring invariably contains a nitrogen atom of a fused imidazole ring and is substituted by a carbonyl, hydroxy or hydroxyimino group. Their favorable antiallergic activity is evidenced by their lack of sedating properties at therapeutic dose levels.

The present invention is concerned with novel imidazoazepines of formula

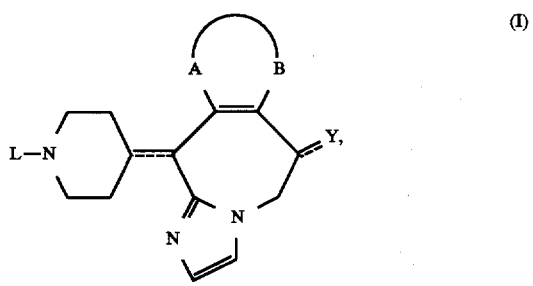

(I)

the pharmaceutically acceptable addition salts and stereochemically isomeric forms thereof, wherein
each of the dotted lines independently represents an optional bond;
—A—B— is a radical of formula
 —X—CH=CH— (a-1);
 —CH=CH—X— (a-2); or
 —CH=CH—CH=CH— (a-3);
X represents O, S or $NR^1$;
$R^1$ represents hydrogen or $C_{1-6}$alkyl;
-----Y is a radical of formula
 =O (b-1);
 —OH (b-2); or
 =N—OH (b-3); and
L represents hydrogen, $C_{1-4}$alkylcarbonyl, $C_{1-4}$alkyloxycarbonyl, phenylcarbonyl, $C_{1-6}$alkyl or $C_{1-6}$alkyl substituted with $C_{1-4}$alkyloxycarbonyl, hydroxycarbonyl, aryl, aryloxy or a radical of formula

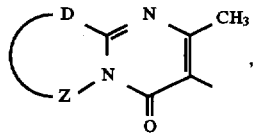

(c)

—D—Z— is —S—CH=CH—, —S—$CH_2$—$CH_2$—, —S—$CH_2$—$CH_2CH_2$—, —CH=CH—CH=CH— or —$CH_2$—$CH_2$—$CH_2$—$CH_2$—; and aryl is phenyl or phenyl substituted with halo, hydroxy or $C_{1-4}$alkyloxy.

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, for example, pentyl and hexyl.

The term pharmaceutically acceptable addition salt as used hereinbefore defines the non-toxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are for example, inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) having acidic properties may be converted in an analogous manner with a suitable base into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine. The term pharmaceutically acceptable addition salts also comprises the solvates which the compounds of formula (I) may form, e.g. the hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention.

Interesting compounds are the compounds of formula (I) having the formula

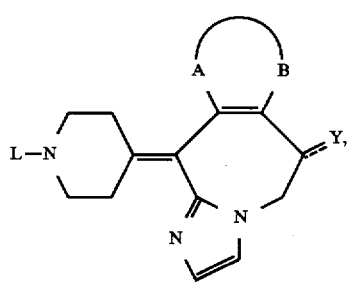

Further interesting compounds are the compounds of formula (I) wherein ═════Y is a radical of formula ═O (b-1).

Another group of interesting compounds are the compounds of formula (I) wherein ═════Y is a radical of formula —OH (b-2).

Still another group of interesting compounds are the compounds of formula (I) wherein ═════Y is a radical of formula ═N—OH (b-3).

Preferred compounds are those compounds of formula (I) having the formula

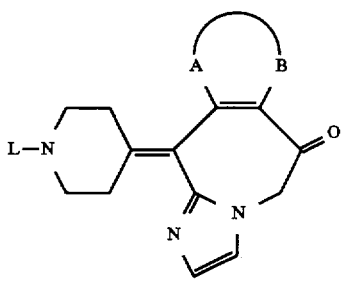

More preferred compounds are those preferred compounds wherein —A—B— is a radical of formula —CH═CH—X— (a-2).

Further preferred compounds are those more preferred compounds wherein X is $C_{1-4}$alkylamino.

Still more preferred compounds are those further preferred compounds wherein L is $C_{1-6}$alkyl.

The most preferred compound is 7, 10-dihydro-7-methyl-10-(1-methyl-4-piperidinylidene)imidazo[1,2-a]pyrrolo[3,2-d]azepin-6(5H)-one, the pharmaceutically acceptable addition salts and the stereochemically isomeric forms thereof.

The compounds of formula (I) wherein ═════Y is a radical of formula ═O (b-1), said compounds being represented by the formula (I-a), can be prepared by reacting an intermediate of formula (II) in the presence of an acid, e.g. trifluoromethanesulfonic acid, and the like.

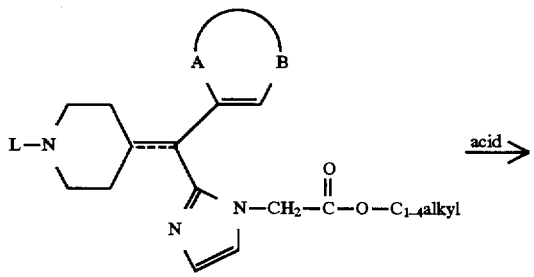

The compounds of formula (I) wherein ═════Y is a radical of formula —OH (b-2), said compounds being represented by the formula (I-b), can be prepared by reacting the compounds of formula (I-a) in the presence of a reducing reagent, e.g. sodium borohydride, in a reaction-inert solvent, e.g. methanol and the like.

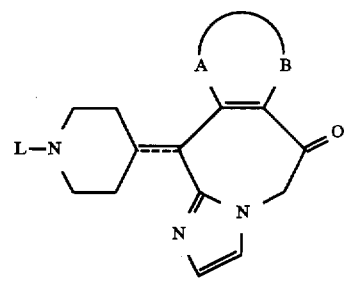

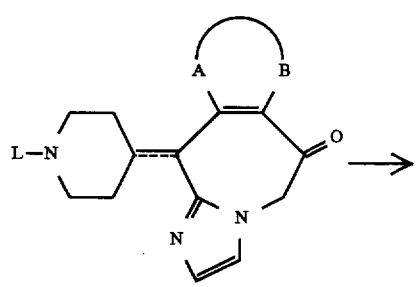

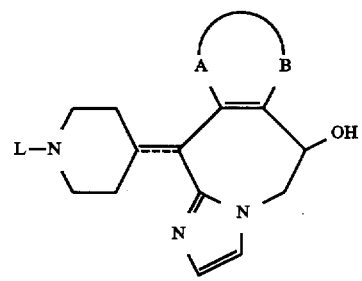

The compounds of formula (I) wherein ═════Y is a radical of formula ═N—OH (b-3), said compounds being represented by the formula (I-c), can be prepared by reacting the compounds of formula (I-a) with hydroxylamine or a salt, e.g. the hydrochloride salt thereof, in a reaction-inert solvent, e.g. pyridine and the like.

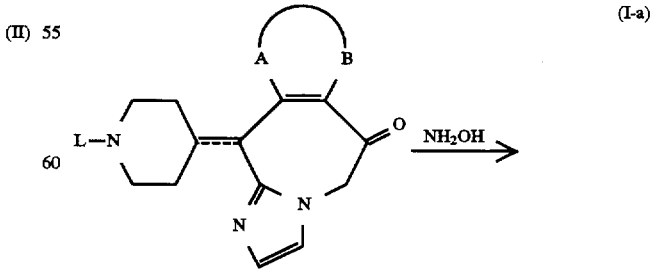

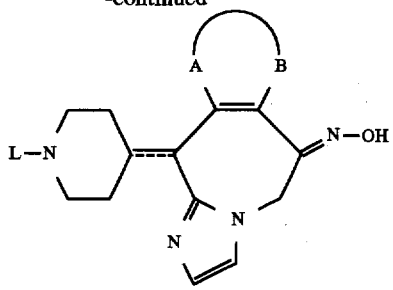
(I-c)

The compounds of formula (I) wherein L is $C_{1-6}$alkyl or $C_{1-6}$alkyl substituted with $C_{1-4}$alkyloxycarbonyl, hydroxycarbonyl, aryl, aryloxy or a radical of formula (c), said compounds being represented by the formula (I-d) and said L by $L^1$, can be prepared by N-alkylating a compound of formula (I) wherein L is hydrogen, said compounds being represented by the formula (I-e), with a reagent of formula $L^1$-W (III).

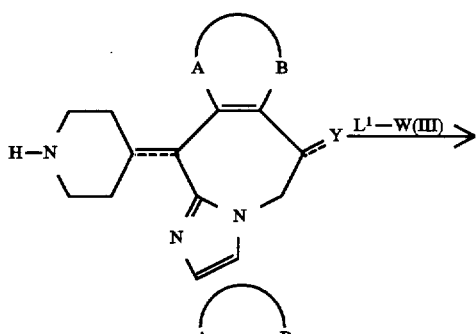

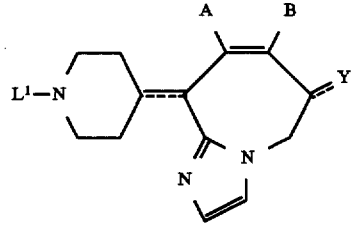

In formula (III) and hereinafter W represents an appropriate leaving group such as, for example, halo, e.g. chloro, bromo and the like; or a sulfonyloxy group such as, for example, methansulfonyloxy, 4-methylbenzenesulfonyloxy and the like. Said N-alkylation reaction can conveniently be conducted in a reaction-inert solvent such as, for example, an aromatic hydrocarbon, an alkanol, a ketone, an ether, a dipolar aprotic solvent, a halogenated hydrocarbon, or a mixture of such solvents. The addition of an appropriate base such as, for example, an alkali or an earth alkaline metal carbonate, hydrogen carbonate, alkoxide, hydride, amide, hydroxide or oxide, or an organic base, such as, for example, an amine, may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

The compounds of formula (I-d) can further be prepared by the addition reaction of a compound of formula (I-e) to an appropriate alkene of formula (IV), wherein $L^2$ is hydrogen, $C_{1-4}$alkyloxycarbonyl, hydroxycarbonyl, aryl, aryloxy or a radical of formula (c), in a reaction-inert solvent, e.g. methanol, and the like:

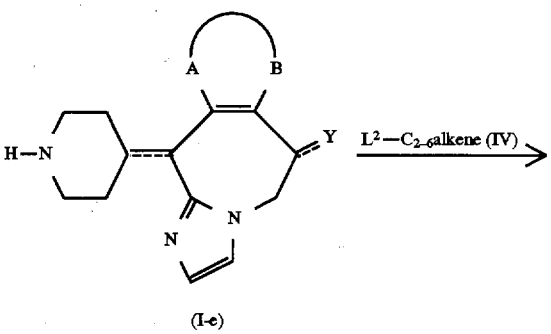

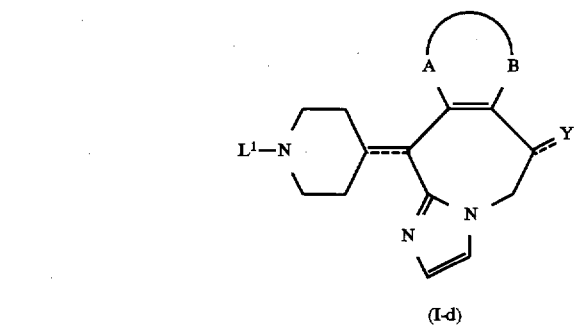

The compounds of formula (I-e) may be prepared by debenzylating a compound of formula

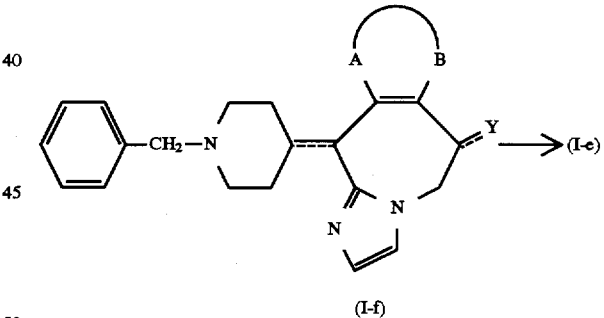

following art known procedures, e.g. catalytic hydrogenation.

The compounds of formula (I-e) wherein ===Y is a radical of formula =O (b-1), said compounds being represented by the formula (I-e-1), can be prepared by hydrolizing an intermediate of formula (V) in the presence of an acid, e.g. hydrobromic acid trifluoroacetic acid and the like.

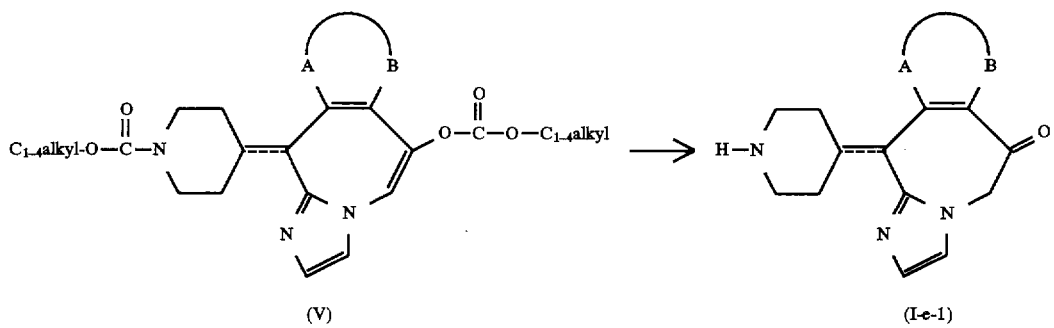

In some instances, the reaction of an intermediate of formula (V) in the presence of an acid may yield a compound of formula

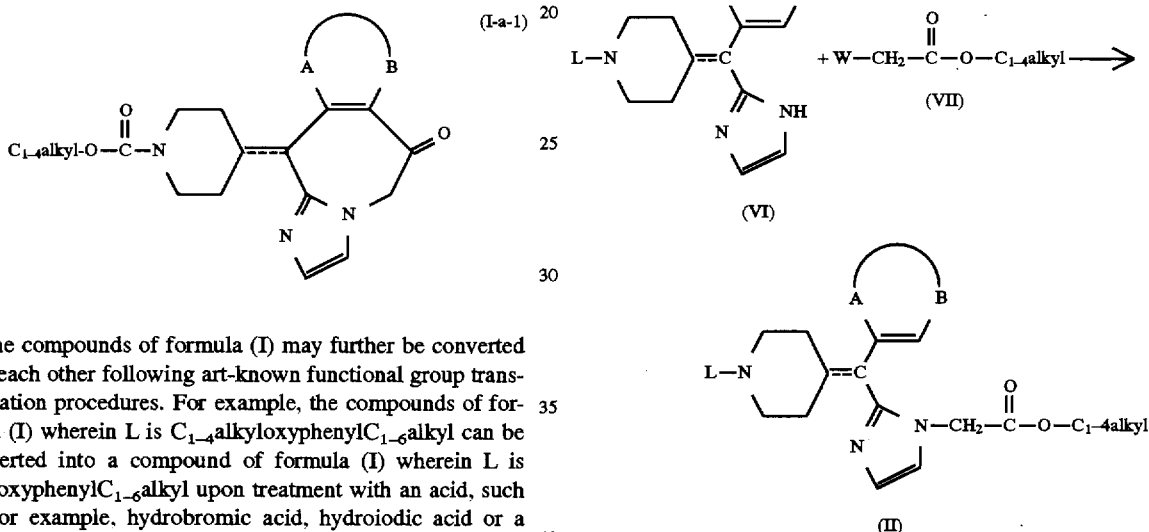

The compounds of formula (I) may further be converted into each other following art-known functional group transformation procedures. For example, the compounds of formula (I) wherein L is $C_{1-4}$alkyloxyphenyl$C_{1-6}$alkyl can be converted into a compound of formula (I) wherein L is hydroxyphenyl$C_{1-6}$alkyl upon treatment with an acid, such as, for example, hydrobromic acid, hydroiodic acid or a Lewis acid, e.g. boron trifluoride, aluminium trichloride and the like.

Pure stereochemically isomeric forms of the compounds of formula (I) may be obtained by the application of art-known procedures. Diastereoisomers may be separated by physical methods such as selective crystallization and chromatographic techniques, e.g. counter current distribution, liquid chromatography and the like. Enantiomers may be separated from each other following art-known resolution methods, for example, by the selective crystallization of the diastereomeric salts with chiral acids. In particular, the enantiomers may be separated by column chromatography using a chiral stationary phase such as a suitably derivatized cellulose, for example, tri(dimethylcarbamoyl)cellulose (Chiralcel OD®) and similar chiral stationary phases. Pure stereochemically isomeric forms may also be derived from the corresponding pure stereochemically isomeric forms of the appropriate starting materials, provided that the reactions occur stereospecifically.

The intermediates of formula (II) can be prepared by reacting an intermediate of formula (VI) with a reagent of formula (VII) in the presence of a base, e.g. sodium hydride, in a reaction-inert solvent, e.g. N,N-dimethylformamide, and the like.

The intermediates of formula (VI) wherein the piperidine is connected with the substituted methyl group by a double bond, said intermediates being represented by the formula (VI-a), can be prepared by dehydrating an intermediate of formula (VIII), e.g. by reaction with an acid, such as, hydrobromic acid, trifluoroacetic acid, methanesulfonic acid, or an acid anhydride, e.g. acetic anhydride.

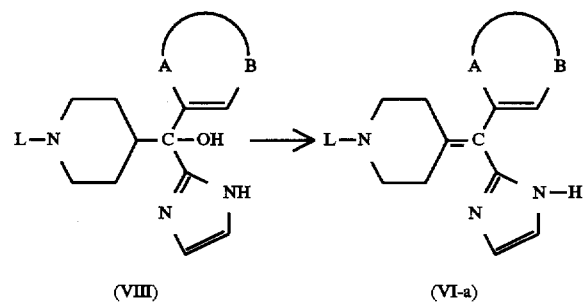

The intermediates of formula (VIII) can be prepared by reacting an intermediate of formula (IX) with a reagent of formula (X) in the presence of butyl lithium and a suitable base, e.g. N-(1-methylethyl)-2-propanamine, in a reaction-inert solvent, e.g. tetrahydrofuran, following art-known procedures.

[Scheme showing compounds (IX) + (X) → ...]

(IX)    (X)

[Structure of compound (VIII)]

(VIII)

The intermediates of formula (VIII) may also be prepared by reacting an intermediate of formula (XI) with a reagent of formula (XII) in the presence of butyl lithium following art-known procedures.

[Scheme: (XI) + (XII) →]

(XI)    (XII)

[Structure of compound (VIII)]

(VIII)

The intermediates of formula (V) can be prepared by reacting a compound of formula (I-a) wherein L is $C_{1-6}$alkyl, said compounds being represented by the formula (I-a-2), with a $C_{1-4}$alkylchloroformate in the presence of a suitable base, e.g. N,N-diethylethanamine, in a reaction-inert solvent, e.g. methylbenzene, and the like.

[Structure of (I-a-2) + Cl—C(=O)—O—$C_{1-4}$alkyl →]

(I-a-2)

-continued

[Structure of compound (V)]

(V)

The compounds of formula (I) as well as the intermediates of formula (V), the pharmaceutically acceptable addition salts and stereochemically isomeric forms thereof possess useful pharmacological properties. In particular they are active antiallergic agents, which activity can clearly be demonstrated by the test results obtained in a number of indicative tests.

Antihistaminic activity can be demonstrated in 'Protection of Rats from Compound 48/80-induced Lethality' test (Arch. Int. Pharmacodyn. Ther., 234, 164–176, 1978);

'Histamine-induced Lethality in Guinea Pigs' test (Arch. Int. Pharmacodyn. Ther., 251, 39–51, 1981);

and the broad antiallergic activity can be demonstrated in 'Passive cutaneous anaphylaxis in Rats' test (Drug Dev. Res., 5, 137–145, 1985) (For some compounds this test has been modified by replacing (compound 48/80 by Ascaris allergens) and the 'Ascaris Allergy in Dogs' test (Arch. Int. Pharmacodyn. Ther., 251, 39–51, 1981 and Drug Dev. Res., 8, 95–102, 1986).

The compounds of the present invention show a broad spectrum antiallergic profile as is evidenced by the results obtained in the diversity of test procedures cited hereinbefore.

Further, the present compounds show inhibitory activity on the migration of eosinophils, the latter being pro-inflammatory cells in allergic reactions.

An important asset of the present compounds is their lack of sedating properties at therapeutic dose levels, a troublesome side effect associated with many antihistaminic and antiallergic compounds. The non-sedating properties of the present compounds can be demonstrated, for example, by the results obtained in studying the sleep-wakefulness cycle of the rat (Psychopharmacology, 97, 436–442, (1989)).

Another interesting feature of the present compounds relates to their fast onset of action and the favorable duration of their action. The latter characteristic may enable the administration of the compound once daily.

In view of their antiallergic properties, the compounds of formula (I) and the intermediates of formula (V), the addition salts and the stereochemically isomeric forms thereof are very useful in the treatment of a broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective mount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administraiion orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g. as a transdermal patch, as a spot-on or as an ointment. Addition salts of the subject compounds, due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I), a pharmaceutically acceptable addition salt form or a stereochemically isomeric form thereof.

The present invention further relates to the compounds of formula (I), the pharmaceutically acceptable addition salt forms and the stereochemically isomeric forms thereof for use as a medicine. In particular, the present invention relates to the subject compounds for use as a medicine for treating warm-blooded animals suffering from allergic diseases.

In general it is contemplated that an effective antiallergic amount would be from about 0.001 mg/kg to about 2 mg/kg body weight, and more preferably from about 0.01 mg/kg to about 0.5 mg/kg body weight.

The following examples are intended to illustrate and not to limit the scope of the present invention in all its aspects.

EXPERIMENTAL PART

A. Preparation of the Intermediates

Example 1 a) A mixture of magnesium turnings (0.34 mol) and bromoethane (0.1 g) in tetrahydrofuran (180 ml) was stirred under $N_2$. 4-Chloro-1-methylpiperidine (0.34 mol) was added dropwise, the mixture was brought till reflux and it was stirred and refluxed for 2 hours. The mixture was cooled till 0° C. 3-Furancarboxaldehyde (0.26 mol) dissolved in tetrahydrofuran was added dropwise at a temperature<20° C. The mixture was brought to room temperature and stirred at room temperature for 1 hour. The mixture was decomposed with an ice/$NH_4Cl$ solution and extracted with 4-methyl-2-pentanone. The organic layer was dried ($MgSO_4$), filtered off and evaporated. The residue was purified by column chromatography over silica gel (eluent: $CH_2Cl_2$/($CH_3OH$/$NH_3$) 95/5). The pure fractions were collected and evaporated, yielding 38.7 g (76%) of product. A sample (1.2 g) was converted into the (Z)-2-butenedioic acid salt (1:1) in 2-propanone, yielding 1.66 g of α-3-furanyl-1-methyl-4-piperidinemethanol (Z)-2-butenedioate(1:1); mp. 150.3° C. (interm. 1).

b) A mixture of the free base of intermediate (1) (0.19 mol) and manganese dioxide (370 g) in trichloromethane (1200 ml) was stirred and refluxed for 18 hours. The mixture was filtered off, washed with trichloromethane and evaporated. The residue was purified on a glass filter over silica gel (eluent: $CH_2Cl_2$/($CH_3OH$/$NH_3$) 95/5). The pure fractions were collected and evaporated, yielding 24 g (65%) of product. A sample (1.5 g) was converted into the (E)-2-butenedioic acid salt (1:1) in ethanol, yielding 1.1 g of (3-furanyl)(1-methyl-4-piperidinyl)methanone (E)-2-butenedioate(1:1); mp. 145.9° C. (interm. 2).

Example 2 a) A mixture of sodium methylate (1.1 mol) in methanol (700 ml) was stirred under $N_2$ at room temperature. 1-Methyl-2-pyrrolacetonitrile (1.1 mol) was added dropwise over a 15 min. period. Then 1-methyl-4-piperidinone (1 mol) was added dropwise over a 15 min. period and the mixture was brought to reflux. The mixture was stirred and refluxed for 3 hours and evaporated. The residue was decomposed with ice water and extracted with dichloromethane. The organic layer was dried ($MgSO_4$), filtered off and evaporated, yielding 214 g (100%) of product. A sample (5 g) was purified on a glass filter over silica gel (eluent: $CH_2Cl_2$/($CH_3OH$/$NH_3$)97/3). The pure fractions were collected and evaporated. The residue was converted into the (E)-2-butenedioic acid salt (1:1) in ethanol, yielding 4.78 g of 1-methyl-α-(1-methyl-4-piperidinylidene)-1H-pyrrole-2-acetonitrile (E)-2-butenedioate (1:1); mp. 165.5° C. (interm. 3).

b) A mixture of the free base of intermediate (3) (0.97 mol) in 2-propanol (1200 ml) was stirred and heated to 40° C. Sodium borohydride (1.94 mol) was added portionwise over a 15 min. period and the reaction mixture was heated to reflux temperature. The mixture was stirred and refluxed for 18 hours. The mixture was cooled, poured into ice water and extracted with 2,2'-oxybispropane. The separated organic layer was dried ($MgSO_4$), filtered and the solvent was evaporated, yielding 196 g (93%) of crude residue. A sample (5 g) was purified over silica gel on a glass filter (eluent: $CH_2Cl_2$/($CH_3OH$/$NH_3$) 97/3). The pure fractions were collected and the solvent was evaporated. The residue was dissolved in ethanol and converted into the (E)-2-butenedioic acid salt (1:1). The precipitate was filtered off and recrystallized from ethanol. The crystals were filtered off and dried, yielding 2.45 g (29.7%) of (±)-1-methyl-α-(1-methyl-1H-pyrrol-2-yl)-4-piperidineacetonitrile (E)-2-butenedioate(1:1); mp. 149.0° C. (interm. 4).

In a similar manner there was prepared:

α-(1-methyl-1H-pyrrol-2-yl)-1-(phenylmethyl)-4-piperidineacetonitrile; mp. 105.5° C. (interm. 25).

c) A mixture of sodium hydroxide (1.6 mol) and benzyltriethylammonium chloride (0.04 mol) in dimethylsulfoxide (340 ml) was stirred with a mechanical stirrer. The free base of intermediate (4) (0.88 mol) dissolved in dimethylsulfoxide (180 ml) was added and air was bubbled through for 6 hours (temperature raised till 55° C.). The mixture was poured into water (2700 ml) and extracted with 4-methyl-2-pentanone. The organic layer was washed twice with water, dried (MgSO4), filtered off and evaporated. The residue was distilled, yielding 83 g (46%) of product. A sample (1 g) was converted into the (E)-2-butenedioic acid salt (1:1) in ethanol, yielding 0.89 g of (1-methyl-4-piperidinyl)(1-methyl-1H-pyrrol-2-yl)methanone (E)-2-butenedioate (1:1); mp. 186.2° C. (interm. 5).

In a similar manner there was prepared:

(1-methyl-1H-pyrrol-2-yl)[1-(phenylmethyl)-4-piperidinyl]methanone (E)-2-butenedioate(1:1); mp. 183.0° C. (interm. 26).

d) A mixture of the free base of intermediate (5) (0.4 mol) in trifluoroacetic acid (1500 ml) and N,N-dimethylformamide (0.1 ml) was stirred and refluxed for 5 days. The mixture was partly evaporated (¾), poured into ice water/K$_2$CO$_3$ and extracted with CH$_2$Cl$_2$. The organic layer was dried (MgSO$_4$), filtered off and evaporated. The residue was distilled, yielding 46 g (56%) of product. A sample (1.5 g) was converted into the (Z)-2-butenedioic acid salt (1:1) in 2-propanone and recrystallized from 2-propanone, yielding 1.52 g of (1-methyl-4-piperidinyl)(1-methyl-1H-pyrrol-3-yl)methanone (Z)-2-butenedioate (1:1); mp. 150.9° C. (interm. 6).

In a similar manner there was prepared:

(1-methyl-1H-3-pyrrolidinyl)[1-(phenylmethyl)-4-piperidinyl]methanone; mp. 145.3° C. (interm. 27).

Example 3

A mixture of N-(1-methylethyl)-2-propanamine (0.23 mol) in tetrahydrofuran (600 ml) was stirred under N$_2$ and cooled till −78° C. A 2.5M solution of butyl lithium in hexane (0.215 mol) was added portionwise at −78° C. The mixture was brought to −40° C. and stirred at this temperature for 15 min. 1-(Diethoxymethyl)imidazole (0.22 mol) dissolved in tetrahydrofuran was added dropwise at −78° C. and the mixture was stirred at −78° C. for 1 hour. The free base of intermediate (6) (0.2 mol) dissolved in tetrahydrofuran was added dropwise at −78° C. and the mixture was stirred at −78° C. for 1 hour. The mixture was brought to room temperature and stirred at room temperature for 2 hours. The mixture was decomposed with water, acetic acid (200 ml) was added and the mixture was stirred at room temperature for 30 min. The mixture was alkalized with K$_2$CO$_3$ and evaporated. The residue was taken up in water and extracted with dichloromethane. The organic layer was dried (MgSO$_4$), filtered off and evaporated. The residue was crystallized from acetonitrile, yielding 46 g (84%) of (±)-α-(1H-imidazol-2-yl)-1-methyl-α-(1-methyl-1H-pyrrol-3-yl)-4-piperidinemethanol; mp. 171.4° C. (interm. 7).

In a similar manner there were prepared:

(±)-α-3-furanyl-α-1H-imidazol-2-yl-1-methyl-4-piperidinemethanol; mp. 189.7° C. (interm. 8);

(±)-α-1H-imidazol-2-yl-1-methyl-α-3-thienyl-4-piperidinemethanol; mp. 173.4° C. (interm. 9);

(±)-α-1H-imidazol-2-yl-1-methyl-α-phenyl-4-piperidinemethanol; mp. 219.4° C. (interm. 10); and (±)-α-1H-imidazol-2-yl-α-(1-methyl-1H-pyrrol-3-yl)-1-(phenylmethyl)-4-piperidinemethanol (interm. 28).

Example 4

Trifluoroacetic acid (700 ml) was stirred at room temperature. Intermediate (7) (0.157 mol) was added portionwise, the mixture was brought till reflux and the mixture was stirred and refluxed for 30 min. The mixture was cooled, partly evaporated (¾), poured into ice/water/K$_2$CO$_3$ and extracted with dichloromethane. The organic layer was dried (MgSO$_4$), filtered off and evaporated. The residue was purified by column chromatography over silica gel (eluent: CH$_2$Cl$_2$/(CH$_3$OH/NH$_3$) 95/5). The pure fractions were collected and evaporated. The residue was crystallized twice from acetonitrile, yielding 23 g (57%) of 4-[1H-imidazol-2-yl(1-methyl-1H-pyrrol-3-yl)methylene]-1-methylpiperidine; mp. 154.8° C. (interm. 11).

In a similar manner there were prepared:

4-[3-furanyl(1H-imidazol-2-yl)methylene]-1-methylpiperidine; mp. 147.2° C. (interm. 12);

4-[1H-imidazol-2-yl(3-thienyl)methylene]-1-methylpiperidine; mp. 174.8° C. (interm. 13);

4-(1H-imidazol-2-ylphenylmethylene)-1-methylpiperidine; mp. 203.9° C. (interm. 14); and 4-[1H-imidazol-2-yl(1-methyl-1H-pyrrol-3-yl)methylene]-1-(phenylmethyl)piperidine; mp. 188.2° C. (interm. 29).

Example 5

A mixture of sodium hydride 60% (0.045 mol) in N,N-dimethylformamide (300 ml) was stirred at room temperature under N$_2$. Intermediate (11) (0.03 mol) dissolved in N,N-dimethylformamide was added dropwise and the mixture was stirred at room temperature for 1 hour. Methyl chloroacetate (0.045 mol) dissolved in N,N-dimethylformamide was added dropwise upon cooling and the mixture was stirred at room temperature for 30 min. The mixture was poured into a NaHCO$_3$ solution and extracted with dichloromethane. The organic layer was dried (MgSO$_4$), filtered off and evaporated. The residue was purified on a glass filter over silica gel (eluent: CH$_2$Cl$_2$/(CH$_3$OH/NH$_3$) 96/4). The pure fractions were collected and evaporated, yielding 7.9 g (80%) of product. A sample (1.5 g) was converted into the (E)-2-butenedioic acid salt (2:3) in ethanol, yielding 1.51 g of methyl 2-[(1-methyl-4-piperidinylidene)(1-methyl-1H-pyrrol-3-yl)methyl]-1H-imidazole-1-acetate (E)-2-butenedioate(2:3); mp. 159.1 ° C. (interm. 15).

In a similar manner there were prepared:

methyl 2-[3-furanyl(1-methyl-4-piperidinylidene)methyl]-1H-imidazole-1-acetate (interm. 16);

methyl 2-[(1-methyl-4-piperidinylidene)-3-thienylmethyl]-1H-imidazole-1-acetate (interm. 17);

methyl 2-[(1-methyl-4-piperidinylidene)phenylmethyl]-1H-imidazole-1-acetate; mp. 105.7° C. (interm. 18); and methyl 2-[(1-methyl-1H-pyrrol-3-yl)[1-(phenylmethyl)-4-piperidinylidene]methyl]-1H-imidazole-1-acetate (interm. 24).

Example 6

A mixture of compound (1) (0.011 mol) and N,N-diethylethanamine (0.033 mol) in methylbenzene (100 ml) was stirred and refluxed. Ethyl chloroformate (0.055 mol) was added dropwise at reflux and the mixture was stirred and refluxed for 1 hour. The mixture was cooled, poured into water/K$_2$CO$_3$ and separated. The aqueous layer was extracted with dichloromethane. The combined organic layers were dried (MgSO$_4$), filtered off and evaporated. The reaction was started again with the residue, the same amounts of ethyl chloroformate, N,N-diethylethanamine and methylbenzene and the same procedure. The residue was purified on a glass filter over silica gel (eluent: $CH_2Cl_2$/ $C_2H_5OH$ 97/3). The pure fractions were collected and evaporated, yielding 4.5 g (95%) of ethyl 4-[6-[(ethoxycarbonyl)oxy]-10H-imidazo[1,2-a]thieno[3,2-d]-azepin-10-ylidene]-1-piperidinecarboxylate (interm. 19).

In a similar manner there were prepared:

ethyl 4-[6-[(ethoxycarbonyl)oxy]-11H-imidazo[2,1-b][3]benzazepin-11-ylidene]-1-piperidinecarboxylate; mp. 149.9° C. (interm. 20); and ethyl 4-[6-[(ethoxycarbonyl)oxy]-7,10-dihydro-7-methylimidazo[1,2-a]pyrrolo-[3,2-d]azepin-10-ylidene]-1-piperidinecarboxylate; mp. 128.9° C. (interm. 23).

Example 7 a) N,N-dimethylformamide (200 ml) was stirred at room temperature under nitrogen and a dispersion sodium hydride 50% in mineral oil (0.113 mol) was added portionwise. 2-Phenylmethyl-1H-imidazole (0.075 mol) was added portionwise and the mixture was stirred for 1 hour at room temperature. Ethyl chloroacetate (0.113 mol) dissolved in N,N-dimethylformamide was added dropwise and the mixture was stirred at room temperature for 30 minutes. The mixture was poured into a $NaHCO_3$ solution and extracted with dichloromethane. The organic layer was dried ($MgSO_4$), filtered off and evaporated. The residue was purified on a glass filter over silica gel (eluent: $CH_2Cl_2$/ $CH_3OH$ 95/5). The pure fractions were collected and evaporated, yielding 16 g (93%) of product. A sample (1 g) was crystallized from 2,2'-oxybispropane/acetonitrile, yielding 0.58 g of methyl 2-(phenylmethyl)-1H-imidazole-1-acetate; mp. 70.8° C. (interm. 21). A mixture of intermediate (21) (0.017 mol) in trifluoromethanesulfonic acid (25 ml) was stirred at 140° C. overnight. The mixture was cooled, poured into a $K_2CO_3$ solution/ice water and extracted with dichloromethane/ethanol. The organic layer was dried ($MgSO_4$), filtered off and evaporated, yielding 1.5 g (45%) of product. This fraction was converted into the (E)-2-butenedioic acid salt (2:1) in ethanol and recrystallized from ethanol, yielding 1.76 g (40.4%) of 11H-imidazo[2,1-b][3]benzazepin-6(5H)-one (E)-2-butenedioate(2:1); mp. 166.3° C. (interm. 22).

B. Preparation of the Final Compounds

Example 8 a) A mixture of intermediate (17) (0.03 mol) in trifluoromethanesulfonic acid (75 ml) was stirred at 105° C. for 6 hours. The mixture was cooled, poured into a ice/$K_2CO_3$ solution and extracted with dichloromethane. The organic layer was dried ($MgSO_4$), filtered off and evaporated. The residue was purified on a glass filter over silica gel (eluent: $CH_2Cl_2$/($CH_3OH$/$NH_3$) 95/5). The pure fractions were collected and evaporated. The residue was stirred up in $CH_2Cl_2$/ $H_2O$/$BaCO_3$. The precipitate was filtered off and the flitrate was separated. The aqueous layer was extracted with dichloromethane. The combined organic layers were dried ($MgSO_4$), filtered off and evaporated. The residue was crystallized from acetonitrile, yielding 5.2 g (58%) of 10-(1-methyl-4-piperidinylidene)-10H-imidazo[1,2-a]thieno[3,2-d]azepin-6(5H)-one; mp. 153.3° C. (comp. 1).

In a similar manner there were prepared:

11-(1-methyl-4-piperidinylidene)-5H-imidazo[2,1-b][3]benzazepin-6(11H)-one (E)-2-butenedioate(2:3); mp. 208.0° C. (comp. 2);

7,10-dihydro-7-methyl-10-(1-methyl-4-piperidinylidene)imidazo[1,2-a]pyrrolo[3,2-d]-azepin-6(5H)-one (E)-2-butenedioate(2:3); mp. 229.1° C. (comp. 3);

10-(1-methyl-4-piperidinylidene)-10H-furo[3,2-d]imidazo[1,2-a]azepin-6(5H)-one (Z)-2-butenedioate(1:2) (comp. 4); and 7,10-dihydro-7-methyl-10-[1-(phenylmethyl)-4-piperidinylidene]imidazo[1,2-a]pyrrolo[3,2-d]azepin-6(5H)-one; mp. 213.5° C. (comp. 22).

b) A mixture of compound (22) (0.037 mol) in methanol (150 ml) was hydrogenated at room temperature (atmospheric pressure) with palladium on activated carbon, palladium content 10% (2 g) as a catalyst. After uptake of $H_2$ (0.7 equiv), the catalyst was filtered off and the filtrate was evaporated. The residue was purified over silica gel on a glass filter (eluent: $CH_2Cl_2$/$CH_3OH$/($CH_3OH$/$NH_3$) 90/5/5, upgrading to 90/0/10). Two fractions were collected and their solvent was evaporated. Both fractions were dissolved in ethanol and converted into the (E)-2-butenedioic acid salt (1:1). The precipitates were filtered off and dried, yielding 5.3 g (36%) of 7,10-dihydro-10-(4-piperidinylidene)imidazo[1,2-a]pyrrolo[3,2-d]azepin-6(5H)-one (E)-2-butenedioate(1:1) (comp. 23) and 5.1 g (35%) of 7,10-dihydro-10-(4-piperidinyl)imidazo[1,2-a]pyrrolo[3,2-d]azepin-6(5H)-one (E)-2-butenedioate(1:1); mp. 243.5° C. (comp. 24).

Example 9 a) A mixture of intermediate (20) (0.014 mol) in a 48% solution of hydrobromic acid in water (80 ml) was stirred and refluxed for 2 hours. The mixture was evaporated. The residue was boiled up in ethanol, yielding 6 g (97%) of 11-(4-piperidinylidene)-11H-imidazo[2,1-b][3]benzazepin-6-(5H)-one dihydrobromide (comp. 5).

In a similar manner there was prepared:

10-(4-piperidinylidene)-10H-imidazo[1,2-a]thieno[3,2-d]azepin-6(5H)-one (E)-2-butenedioate (1:1) (comp. 6).

b) A mixture of intermediate (23) (0.02 mol) in trifluoroacetic acid (150 ml) was stirred and refluxed for 18 h. The mixture was evaporated, the residue was poured into ice/water/$K_2CO_3$ and extracted with dichloromethane. The organic layer was dried ($MgSO_4$), filtered off and evaporated. The residue was purified on a glass filter over silica gel (eluent: $CH_2Cl_2$/$C_2H_5OH$ 96/4). The pure fractions were collected and evaporated. The residue was crystallized from a mixture of acetonitrile and 2,2-oxybispropane, yielding: 5.3 g (75%) of ethyl 4-(5,6,7,10-tetrahydro-7-methyl-6-oxoimidazo[1,2-a]pyrrolo[3,2-d]azepin-10-ylidene)-1-piperidinecarboxylate; mp. 146.6° C. (comp. 26)

Example 10

A mixture of 6-(2-chloroethyl)-7-methyl-5H-thiazolo[3,2-a]pyrimidin-5-one monohydrochloride (0.013 mol), the free base of compound (5) (0.01 mol), sodium carbonate (0.024 mol) and potassium iodide (10 mg) in 4-methyl-2-pentanone (200 ml) was stirred and refluxed for 36 hours. The mixture was cooled and evaporated. The residue was taken up in $CH_2Cl_2$/$H_2O$ and separated. The aqueous layer was extracted with dichloromethane. The organic layer was dried ($MgSO_4$), filtered off and evaporated. The residue was purified on a glass filter over silica gel (eluent: $CH_2Cl_2$/ ($CH_3OH$/$NH_3$) 97/3). The pure fractions were collected and evaporated. The residue was crystallized from acetonitrile, yielding 2.46 g (52%) of 11-[1-[2-(7-methyl-5-oxo-11H-thiazolo-[3,2-a]pyrimidin-6-yl)ethyl]-4-piperidinylidene]-5H-imidazo[2,1-b][3]benzazepin-6(5H)-one; mp. 221.6° C. (comp. 7).

In a similar manner there were prepared:
11-[1-[3-(4-fluorophenoxy)propyl]-4-piperidinylidene]-11H-imidazo[2,1-b][3]benzazepin-6(5H)-one (E)-2-butenedioate (1:1) hemihydrate; mp. 201.8° C. (comp. 8);
11-[1-[2-(4-methoxyphenyl)ethyl]-4-piperidinylidene]-11H-imidazo[2,1-b][3]benzazepin-6(5H)-one (E)-2-butenedioate (1:1) hemihydrate; mp. 157.9° C. (comp. 9);
10-[1-[2- (4-methoxyphenyl)ethyl]-4-piperidinylidene]-10H-imidazo[1,2- a]thieno[3,2-d]azepin-6(5H)-one (E)-2-butenedioate (1:1) hemihydrate; mp. 174.9° C. (comp. 10);
10-[1-[3-(4-fluorophenoxy)propyl]-4-piperidinylidene]-10H-imidazo[1,2-a]thieno-[3,2-d]azepin-6(5H)-one (E)-2-butenedioate (1:1) hemihydrate; mp. 177.9° C. (comp. 11);
10-[1-[2-(7-methyl-5-oxo-5H-thiazolo[3,2-a]pyrimidin-6-yl)ethyl]-4-piperidinylidene]-10H-imidazo[1,2-a]thieno[3,2-d]azepin-6(5H)-one (comp. 12); and
7,10-dihydro-7-methyl-10-[1-[2-(7-methyl-5-oxo-5H-thiazolo[3,2-a]pyrimidin-6-yl)ethyl]-4-piperidinylidene]imidazo[1,2-a]pyrrolo[3,2-d]azepine-6(5H)-one; mp. 248.2° C. (comp. 25)

Example 11

Methyl-2-propenoate (0.012 mol) was added dropwise upon stirring to a mixture of compound (5) (0.01 mol) in methanol (100 ml) at room temperature and the mixture was stirred at room temperature for 6 hours. The mixture was evaporated, the residue was taken up in $H_2O/CH_2Cl_2$ and separated. The aqueous layer was extracted with dichloromethane. The organic layer was dried ($MgSO_4$), filtered off and evaporated. The residue was purified on a glass filter over silica gel (eluent: $CH_2Cl_2/CH_3OH$ 95/5). The pure fractions were collected and evaporated. The residue was converted into the cyclohexanesulfamic acid salt (1:2) in 2-propanone, yielding 1.32 g (18%) of methyl 4-(5,6-dihydro-6-oxo-11H-imidazo[2,1-b][3]benzazepin-11-ylidene)-1-piperidine-propanoate hemihydrate cyclohexylsulfamate (1:2) (comp. 13).

In a similar manner there was prepared:
methyl 4-(5,6-dihydro-6-oxo-10H-imidazo[1,2-a]thieno[3,2-d]azepin-10-ylidene)-1-piperidinepropanoate; mp. 123.7° C. (comp. 14).

Example 12

A mixture of compound (10) (0.007 mol) in a 48% solution of hydrobromic acid in water (100 ml) was stirred and refluxed for 1 hour. The mixture was evaporated, the residue was taken up in water, alkalized with $K_2CO_3$ and extracted with dichloromethane. The organic layer was dried, filtered off and evaporated. The residue was purified by column chromatography over silica gel (eluent $CH_2Cl_2/$ ($CH_3OH/NH_3$) 95/5). The pure fractions were collected and evaporated. The residue was converted into the (E)-2-butenedioic acid salt (1:1) in ethanol. The precipitate was filtered off and dried, yielding 1.17 g (32%) of 10-[1-[2-(4-hydroxyphenyl)ethyl]-4-piperidinylidene]-10H-imidazo[1,2-a]thieno[3,2-d]azepin-6(5H)-one (E)-2-butenedioate (1:1) (comp. 15).

In a similar manner there was prepared:
11-[1-[2-(4-hydroxyphenyl)ethyl]-4-piperidinylidene]-11H-imidazo[2,1-b][3]benzazepin-6(5H)-one (E)-2-butenedioate (1:1); mp. 227.9° C. (comp. 16).

Example 13

A mixture of compound (1) (0.025 mol) in methanol (100 ml) was stirred and cooled. Sodium borohydride (0.05 mol) was added portionwise over a 15 min. period and the mixture was stirred at room temperature for 1 hour. The mixture was evaporated at a temperature<40° C. The residue was taken up in water and extracted with dichloromethane. The organic layer was dried ($MgSO_4$), filtered off and evaporated. The residue was boiled up in acetonitrile, yielding 7.5 g (100%) of (±)-6,10-dihydro-10-(1-methyl-4-piperidinylidene)-5H-imidazo[1,2-a]thieno[3,2-d]azepin-6-ol; mp. 230.3° C. (comp. 17).

In a similar manner there were prepared:
(±)-6,11-dihydro-11-(1-methyl-4-piperidinylidene)-5H-imidazo[2,1-b][3]benzazepin-6 -ol; mp. 138.0° C. (comp. 18); and
(±)-5,6,7,10-tetahydro-7-methyl-10-(1-methyl-4-piperidinylidene)imidazo[1,2-a]pyrrolo[3,2-d]azepin-6-ol ethanolate (1:1).(E)-2-butenedioate (1:1); mp. 191.4° C. (comp. 19).

Example 14

A mixture of compound (1) (0.01 mol) and hydroxylamine monohydrochloride (0.02 mol) in pyridine (20 ml) was stirred and refluxed for 1 hour. The mixture was evaporated, the residue was taken up in water, alkalized with $K_2CO_3$ and extracted with dichloromethane. The organic layer was dried ($MgSO_4$), filtered off and evaporated. The residue was crystallized from acetonitrile, yielding 3 g (96%) of (E+Z)-10-(1-methyl-4-piperidinylidene)-10H-imidazo[1,2-a]thieno[3,2-d]azepin-6(5H)-one oxime; mp. 187.5° C. (comp. 20).

In a similar manner there was prepared:
7,10-dihydro-7-methyl-10-(1-methyl-4-piperidinylidene) imidazo[1,2-a]pyrrolo[3,2-d]azepin-6(5H)-one, oxime; mp. 206.9° C. (comp. 21).

C. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I) or a compound of formula (V), a pharmaceutically acceptable acid addition salt or a stereochemically isomeric form thereof.

Example 15

Oral Drops 500 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50, l providing an oral drop solution comprising 10 mg/ml of the A.I. The resulting solution is filled into suitable containers.

Example 16

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I.

The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 17

Capsules 20 g of the A.I., 6 g sodium lauryl sulfate, 56 g starch, 56 g lactose., 0.8 g colloidal silicon dioxide, and 1.2 g magnesium stearate are vigorously stirred together. The resulting mixture is subsequently filled into 1000 suitable hardened gelatin capsules, each. comprising 20 mg of the A.I.

Example 18

Film-coated Tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterorex®). The whole is mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

D. Pharmacological Example

Example 19

The ED$_{50}$ values (mg/kg) in the test "Protection of Rats from Compound 48/80 induced Lethality" were found to be equal to or below 0.16 for the compounds 1, 3, 4, 6, 10, 11, 12, 15, 22, 23, 25 and 26 and for intermediate 23.

We claim:

1. A compound having the formula (I)

a pharmaceutically acceptable addition salt or a stereochemically isomeric form thereof, wherein
each of the dotted lines independently represents an optional bond;
—A—B— is a radical of formula
  —X—CH=CH— (a-1);
  —CH=CH—X— (a-2); or
  —CH=CH—CH=CH— (a-3);
X represents O, S or NR$^1$;
R$^1$ represents hydrogen or C$_{1-6}$alkyl;
-----Y is a radical of formula
  =O (b-1);
  —OH (b-2); or
  =N—OH (b-3); and
L represents hydrogen, C$_{1-4}$alkylcarbonyl, C$_{1-4}$alkyloxycarbonyl, phenylcarbonyl, C$_{1-6}$alkyl or C$_{1-6}$alkyl substituted with C$_{1-4}$alkyloxycarbonyl, hydroxycarbonyl, aryl, aryloxy or a radical of formula (c)

—D—Z— is —S—CH=CH—, —S—CH$_2$—CH$_2$—, —S—CH$_2$—CH$_2$CH$_2$—, —CH=CH—CH=CH— or —CH$_2$—CH$_2$—CH$_2$—CH$_2$—; and
aryl is phenyl or phenyl substituted with halo, hydroxy or C$_{1-4}$alkyloxy.

2. A compound according to claim 1 having the formula

3. A compound according to claim 2 wherein —A—B— is a radical of formula —CH=CH—X— (a-2).

4. A compound according to claim 3 wherein said compound is 7,10-dihydro-7-methyl-10-(1-methyl-4-piperidinylidene)imidazo[1,2-a]pyrrolo[3,2-d]azepin-6(5H)-one, a pharmaceutically acceptable addition salt or a stereochemically isomeric forms thereof.

5. A pharmaceutical composition comprising as an active ingredient a therapeutically effective amount of a compound as defined in claim 1 and a pharmaceutically acceptable carrier.

6. A compound having the formula

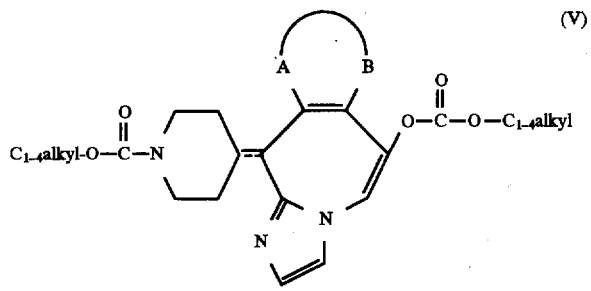

an addition salt or a stereochemically isomeric form thereof, wherein —A—B— is as defined in claim 1.

7. A compound having the formula

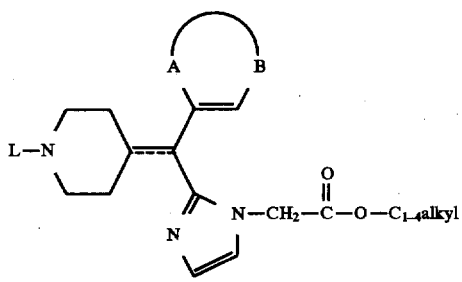

an addition salt or a stereochemically isomeric form thereof, wherein —A—B— and L are as defined in claim 1.

8. A pharmaceutical composition comprising as an active ingredient a therapeutically effective amount of a compound as defined in claim 2 and a pharmaceutically acceptable carrier.

9. A pharmaceutical composition comprising as an active ingredient a therapeutically effective amount of a compound as defined in claim 3 and a pharmaceutically acceptable carrier.

10. A pharmaceutical composition comprising as an active ingredient a therapeutically effective amount of a compound as defined in claim 4 and a pharmaceutically acceptable carrier.

11. A method of treating allergic diseases in patients suffering from the same which comprises administering to such patients a therapeutically effective amount of a compound as defined in claim 1.

12. A method of treating allergic diseases in patients suffering from the same which comprises administering to such patients a therapeutically effective amount of a compound as defined in claim 2.

13. A method of treating allergic diseases in patients suffering from the same which comprises administering to such patients a therapeutically effective amount of a compound as defined in claim 3.

14. A method of treating allergic diseases in patients suffering from the same which comprises administering to such patients a therapeutically effective amount of a compound as defined in claim 4.

* * * * *